(12) United States Patent
Saguy et al.

(10) Patent No.: US 7,519,487 B2
(45) Date of Patent: Apr. 14, 2009

(54) SYSTEM AND METHOD FOR DEPTH DETERMINATION OF CRACKS IN CONDUCTING STRUCTURES

(75) Inventors: Hagit Saguy, Kiryat Biyalik (IL); Daniel Rittel, Haifa (IL)

(73) Assignee: Technion Research and Development Foundation Ltd., Haifa (IL)

( * ) Notice: Subject to any disclaimer, the term of this patent is extended or adjusted under 35 U.S.C. 154(b) by 0 days.

(21) Appl. No.: 11/714,271

(22) Filed: Mar. 6, 2007

(65) Prior Publication Data

US 2007/0250277 A1 Oct. 25, 2007

Related U.S. Application Data

(60) Provisional application No. 60/778,845, filed on Mar. 6, 2006.

(51) Int. Cl.
*G01R 19/00* (2006.01)
(52) U.S. Cl. .......................... 702/64; 73/799; 324/233; 324/240; 324/715
(58) Field of Classification Search .................. 702/64; 324/233, 240, 242, 713, 715–718, 722–724; 73/799, 808, 775, 772, 763, 768, 774, 762, 73/835
See application file for complete search history.

(56) References Cited

U.S. PATENT DOCUMENTS

| 4,924,708 A | * | 5/1990 | Solomon et al. | 73/799 |
|---|---|---|---|---|
| 5,202,641 A | * | 4/1993 | Unvala | 324/715 |
| 5,258,708 A | * | 11/1993 | Sadeghi et al. | 324/240 |
| 5,610,517 A | * | 3/1997 | Ma et al. | 324/233 |
| 5,861,559 A | * | 1/1999 | Solomon et al. | 73/799 |
| 5,864,229 A | * | 1/1999 | Lund | 324/240 |
| 6,218,846 B1 | * | 4/2001 | Ludwig et al. | 324/713 |
| 6,476,624 B1 | * | 11/2002 | Chuman et al. | 324/718 |
| 7,185,545 B2 | * | 3/2007 | Wright, III | 73/799 |
| 2007/0007955 A1 | * | 1/2007 | Goldfine et al. | 324/240 |

FOREIGN PATENT DOCUMENTS

GB 2161936 1/1986

OTHER PUBLICATIONS

Johnson, W.C., Transmission Lines and Networks, McGraw-Hill, New York, 1950, p. 58-80.
Collins, R. , et al., The A.C. Field around a Plane Semi-Elliptical Crack in a Metal Surface, 13th Symposium on NDE, San Antonio, Texas, 1981, pp. 470-479.

(Continued)

*Primary Examiner*—Carol S Tsai
(74) *Attorney, Agent, or Firm*—Browdy and Neimark, P.L.L.C.

(57) ABSTRACT

The alternating current potential drop ACPD technique is used to monitor surface cracks in electrical conductors. At high frequencies, the current flows in a superficial skin layer. Two distinct solutions are currently available for the thin and thick skin cases. However, there is no general solution that bridges these two modes in a seamless fashion. A numerical model is used to analyze the ACPD of a surface crack with uniform depth. A general solution is given that bridges the thin and thick skin solutions, which closely matches the numerical results, irrespective of the skin thickness. Methods for estimating depth of cracks are provided for surface penetrating cracks and back cracks.

7 Claims, 6 Drawing Sheets

OTHER PUBLICATIONS

Bowler, Nicola, Model-Based Characterization of Homogenous Metal Plates by Four Point Alternating Current Potential Drop Measurements, IEEE transactions on magnetics, vol. 41, No. 6, Jun. 2005, pp. 2102-2110.

Bowler, Nicola, Theory of four-point alternating current potential drop measurements on a metal half-space J. Phys D: Applied Phys. 39 (2006) 584-589.

Michael, D.H., et al., The AC field around a plane crack in a metal surface when the skin depth is large, Journal of Non-Destructive Evaluation, vol. 3, No. 1, p. 19-24, Mar. 1982.

Mirshekar-Syahkal, D., et al., The Influence of Skin Depth on Crack Measurement by the ac Field Technique, Journal of Nondestructive Evaluation, vol. 3, No. 2, 1982.

Lugg, M.C., Data interpretation in ACPD crack inspection, NDT International vol. 22 No. 3, Jun. 1989, pp. 149-154.

Dover, W.D. et al., Review of Developments in ACPD and ACFM, British journal of NDT, vol. 33, No. 3 Mar. 1991, pp. 121-127.

Okada, Hiroshi, et al., A Computational Approach to Determining the Depth of Surface Flaws by the ACPD Technique, Engineering Fracture Mechanics vol. 43, No. 6, pp. 911-921, 1992.

Dover, W.D., et al., a.c. Field Measurement—Theory and Practice, University College London, Gower Street, London, W.C.1, U.K, pp. 222 255.

Dover, W.D., et al., The Measurement of Surface Breaking Cracks by the Electrical Systems ACPD/ADFM, Fatigue-&-fracture-of-Engineering-Materials-&-Structures. vol. 17, No. 12; Dec. 1994; p. 1485-1492.

Collins, R., et al., The Use of AC Field Measurements for Nondestructive Testing, London Centre for Marine Technology, University College London, London, U.K., Academic Press Inc. (London) Ltd. 1985, pp. 210-223.

* cited by examiner

SYSTEM AND METHOD FOR DEPTH DETERMINATION OF CRACKS IN CONDUCTING STRUCTURES

This present application claims the benefit of earlier U.S. provisional patent application Ser. No. 60/778,845 filed on Mar. 6, 2006 by Hagit et al. and entitled: "Electrocal tomography of hidden flowsnin conductors using the alternating current potential drop".

FIELD OF THE INVENTION

The present invention is related generally to the field of nondestructive testing and specifically to alternating current potential drop (ACPD) technique for detecting cracks in conducting samples.

BACKGROUND OF THE INVENTION

Nondestructive testing (NDT) is the examination of an object or material in any manner that will not impair its future usefulness. NDT is performed to evaluate the internal and/or external condition of materials, components and structures without any damage to them.

In the industry NDT technologies are used to help ensure the integrity and reliability of products being provided to the end users. The NDT process may range anywhere from a simple visual inspection to an intricate ultrasonic characterization of microstructures at ambient temperature or a radiography examination of parts during a manufacturing operation. Although less accurate than destructive testing, NDT is much more cost-effective and therefore widely spread in various industries including: automotive, aviation/aerospace, construction, manufacturing, nuclear engineering and petrochemicals.

Although many NDT methods are available, 6 are currently most common:

Visual Inspection—this is the most common inspection method. Work is done using fiberscopes, borescopes, magnifying glasses and mirrors. Portable video inspection unit with zoom allows inspection of large tanks and vessels, railroad tank cars, sewer lines; Robotic crawlers permit observation in hazardous or tight areas, such as air ducts, reactors and pipelines.

Liquid Penetrant Inspection—A liquid with high surface wetting characteristics is applied to the surface of the part and allowed time to seep into surface breaking defects. Then, excess liquid is removed from the surface of the part. A developer (powder) is applied to pull the trapped penetrant out the defect and spread it on the surface where it can be seen. The penetrant used is often loaded with a fluorescent dye and visual inspection is done under UV light to increase test sensitivity as the final step in the process.

Magnetic Particle Inspection—The part is first magnetized, and then finely milled iron particles coated with a dye pigment are applied to the specimen. These particles are attracted to magnetic flux leakage fields and will cluster to form an indication directly over the discontinuity. This indication can be visually detected under proper lighting conditions.

Film Radiography—The part is placed between the radiation source and a piece of photographic film. The part will stop some of the radiation. Thicker and denser area will stop more of the radiation. The film darkness (density) will vary with the amount of radiation reaching the film through the test object, revealing hidden cracks and holes.

Eddy Current Testing—uses electromagnetic induction to detect flaws in conductive materials; the Cracks cause disturbances in the magnetic field revealing any defects. This method has several limitations, among them: the surface of the material must be accessible, the finish of the material may cause bad readings, the depth of penetration into the material is limited, and flaws that lie parallel to the probe may be undetectable.

Ultrasonic Inspection (Pulse-Echo)—this method uses High frequency sound waves introduced into a material and reflected back from surfaces or flaws. The reflected sound energy is displayed versus time, and the inspector can visualize a cross section of the specimen showing the depth of features that reflect sound.

The alternating current potential drop (ACPD) is a well-established electromagnetic technique for sizing surface-breaking defects in metals. It is particularly suited to obtaining detailed crack profiles and to monitoring crack growth or initiation. It is a contacting method which requires surface cleaning. ACPD works by inputting an alternating current into the sample so it flows across the defect. The current is normally directly injected, but can be induced. A voltage probe then measures surface potential differences.

By comparing potential differences across the crack with a reference value, the extra path length caused by the defect can be estimated, giving a value for the crack depth.

The alternating current potential drop (ACPD) technique is known in the art and is used to monitor surface cracks in electrical conductors. At high frequencies, the current flows in a superficial skin layer. Two distinct solutions are currently available for the thin and thick skin cases. However, there is no general solution that bridges these two modes in a seamless fashion. Moreover, techniques used in the art do not allow detection locating and characterization of flaws below the surface, or on the surface other than the inspected surface.

U.S. Pat. No. 5,258,708; to Sadeghi et al.; entitled "Methods and apparatus for non-destructive testing of materials with eddy currents" discloses a non-destructive method for the detection of surface cracks in metals, wherein an eddy current is induced in the surface region of a workpiece under test, at a frequency sufficiently high to generate an alternating magnetic field solely in the skin region of the workpiece. That alternating surface magnetic field is interrogated by means of a relatively small electro-magnetic induction sensor, having regard to the overall area of the induced magnetic field. The sensor provides a voltage output which is analyzed, preferably in real time, to yield an indication sensor. Also described is a probe for performing such a method.

U.S. Pat. No. 5,202,641; to Unvala Bhikhu; entitled "Method, test probe and apparatus for the measurement of alternating current potential drop by confining test current to a skin region of a test specimen"; discloses an ACPD method and system of measurement on specimen surface—using skin effect frequency and lateral current restriction by passing same current over and close to surface.

Patent GB 2161936A; to Graham at al.; entitled "alternating current potential drop crack detection"; discloses an alternating current potential drop crack detection system having differential input operational amplifier coupled to probes in test area and in reference area.

Background information related to flow of alternating current in conductors may be found in papers by Nicola Bowler: Nicola Bowler; J. Phys. D: Appl. Phys. Vol. 39 584-589 (2006); "Theory of four-point alternating current potential drop measurements on a metal half-space"; and Nicola Bowler; IEEE transactions on magnetics, vol. 41, no. 6, June 2005; "Model-Based Characterization of Homogeneous Metal Plates by Four-Point Alternating Current Potential Drop Measurements"

More background information may be found in the following references:

[1] R. Collins, W. D. Dover, and D. H. Michael, in Nondestructive Testing, edited by R. S. Sharpe (Academic, New York, 1985), Chap. 5.
[2] R. Collins, W. D. Dover, and K. B. Ranger, 13th Symposium on NDE, San Antonio, Tex., 1981.
[3] W. D. Dover, R. Collins, and D. H. Michael, Br. J. Non-Destr. Test. 33, 121 (1991).
[4] W. C. Johnson, Transmission Lines and Networks (McGraw-Hill, New York, 1950), pp. 58-80.
[5] W. D. Dover and C. C. Monahan, Fatigue Fract. Eng. Mater. Struct. 17, 1485 (1994).
[6] W. D. Dover, F. D. Charlesworth, K. A. Taylor, R. Collins, and D. H. Michael, in The Measurement of Crack Length and Shape During Fracture and Fatigue, edited by C. J. Beevers (Cradley Heath, England, 1980).
[7] O. Hirsoshi, Z. Wei, and N. A. Satya, Eng. Fract. Mech. 43, 911 (1992).
[8] M. C. Lugg, NDT Int. 22, 149 (1989).
[9] D. Mirshekar-Syahkal, R. Collins, and D. H. Michael, J. Nondestruct. Eval. 3, 65 (1982).
[10] D. H. Michael and R. Collins, J. Nondestruct. Eval. 3, 19 (1982).
[11] ANSYS, Electromagnetic Toolbox [8], 2004, ANSYS Inc.

SUMMARY OF THE INVENTION

The present invention provides a system and method for detecting and determining the depth of cracks in conducting structures.

The paper entitled "Bridging thin and thick skin solutions for alternating currents in cracked conductors"; to H. Saguy and D. Rittel; published online 17 Aug. 2005 in Appl. Phys. Lett. 87, 084103 (2005); and incorporated herein by reference; provides a numerical model which is used to analyze the ACPD of a surface crack with uniform depth, and a general analytical solution is given that bridges the thin and thick skin solutions, which closely matches the numerical results, irrespective of the skin thickness.

According to an aspect of the current invention, a general solution is given that bridges the thin and thick skin solutions, which closely matches the numerical results, irrespective of the skin thickness.

According to exemplary embodiments of the invention, methods for estimating depth of cracks are provided for surface penetrating cracks and back cracks.

According to an exemplary embodiment of the invention, a method for estimation of the depth of surface penetrating crack is provided comprising the steps of:

applying alternating current to a sample;
measuring voltage drop $V_1(f)$ between two probes separated by a gap of distant $\Delta$ and making electrical contact with the surface of the sample for at least one frequency f, wherein said probes are located remove from the surface penetrating crack;
measuring voltage drop $V_2(f)$ between two probes separated by a gap of distance $\Delta$ and making electrical contact with said surface of said sample, for at least same frequency f, wherein said probes are located at different sides of said surface penetrating crack;

calculating $\delta$ based on electrical parameters of said sample's material; and
estimating the depth d of said surface penetrating crack from the equation:

$$\frac{V_2(f)}{V_1(f)} = \frac{\Delta + 2d - F_1(\Delta, \delta) - F_2(d, \delta)}{\Delta},$$

wherein $$F_1(\Delta, \delta) = \Delta \cdot \exp\left[-\frac{\Delta/2 + \delta}{\delta}\right],$$

and $$F_2(d, \delta) = 2 \cdot d \cdot \exp\left[-\frac{d + \delta}{\delta}\right],$$

and wherein:

$$\delta = \frac{1}{(\pi \mu_r \mu_0 \sigma f)^{1/2}},$$

where $\mu_r$ is the relative magnetic permeability; $\mu_0$ is the magnetic permeability of free space; $\sigma$ is the electric conductivity; f is the frequency.

In some embodiments the step of estimating the depth d of said surface penetrating crack from the equation $$\frac{V_2}{V_1} = \frac{\Delta + 2d - F_1(\Delta, \delta) - F_2(d, \delta)}{\Delta}$$

comprises numerically solving said equation.

In some embodiments the method further comprises:
scanning said two probes separated by a gap of distant $\Delta$ and making electrical contact with said surface of said sample along said surface, while measuring said voltage drop;
determining the location of said surface penetrating crack by finding a maximum of said measured voltage drop; and
assigning the value $V_2(f_i)$ to the said maximum of said measured voltage drop.

In some embodiments the method further comprises the steps of:
measuring voltage drop $V_1(f_i)$ between probes separated by a constant gap and making electrical contact with said surface of said sample, for plurality of frequencies $f_i$, where probes are located remove from the bottom crack;
measuring voltage drop $V_2(f_i)$ between probes separated by a constant gap and making electrical contact with said surface of said sample, for same plurality of frequencies $f_i$, where probes are located at different sides of said surface penetrating crack; and
estimating the depth d of said surface penetrating crack from the set of equations:

$$\frac{V_2(f)}{V_1(f)} = \frac{\Delta + 2d - F_1(\Delta, \delta) - F_2(d, \delta)}{\Delta}$$

evaluated for frequencies $f_i$.

In some embodiments the step of estimating the depth d of said surface penetrating crack comprises fitting a single fifing parameter d to said set of equations.

According to another exemplary embodiment of the current invention, a method for estimation of the depth of a crack located near the bottom surface of a sample is provided comprising the steps of:

applying alternating current to a sample.
  measuring voltage drop $v_1(f_i)$ between two probes separated by a gap of distant $\Delta$ and making electrical contact with the top surface of the sample for plurality of frequencies $f_i$ wherein said probes are located remove from the bottom crack;
  measuring voltage drop $v_2(f_i)$ between two probes separated by a gap of distant $\Delta$ and making electrical contact with said top surface of the sample for the same plurality of frequencies $f_i$ wherein said probes are located above different sides of the bottom crack;
  for each frequency $f_i$, calculating the ratio $[v_2/v_1](f_i)$ by dividing $v_2(f_i)$ by $v_1(f_i)$;
  for each frequency $f_i$, calculating $\delta(f_i)$ based on electrical parameters of sample material;
  plotting the ratio $[v_2/v_1](f_i)$ as a function of $\delta(f_i)$;
  from said plot of the ratio $[v_2/v_1](f_i)$ as a function of $\delta(f_i)$, estimating the value of $\delta_0$ where the ratio $v_2/v_1$ start departing from horizontal; and
  calculating the estimated depth d' of back crack from the equation: $d'=t-2\,\delta_0$ wherein t is the sample thickness.

In some embodiments the method further comprises the steps of:

scanning said two probes separated by a gap of distant $\Delta$ and making electrical contact with said top surface of said sample along said top surface, while measuring said voltage drop;
  determining the location of said crack by finding a maximum of said measured voltage drop; and
  assigning the value $v_2(f)$ to the said maximum of said measured voltage drop.

It should be noted that that the ratio $V_2/V$, and $V_2/v_1$ must be equal or greater than 1. Any other case is not physical.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings.

DESCRIPTION OF THE PREFERRED EMBODIMENTS

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

The drawings are generally not to scale. For clarity, non-essential elements were omitted from some of the drawings. In discussion of the various figures described herein below, like numbers refer to like parts.

As used herein, an element or step recited in the singular and proceeded with the word "a" or "an" should be understood as not excluding plural elements or steps, unless such exclusion is explicitly recited.

Figure 1:
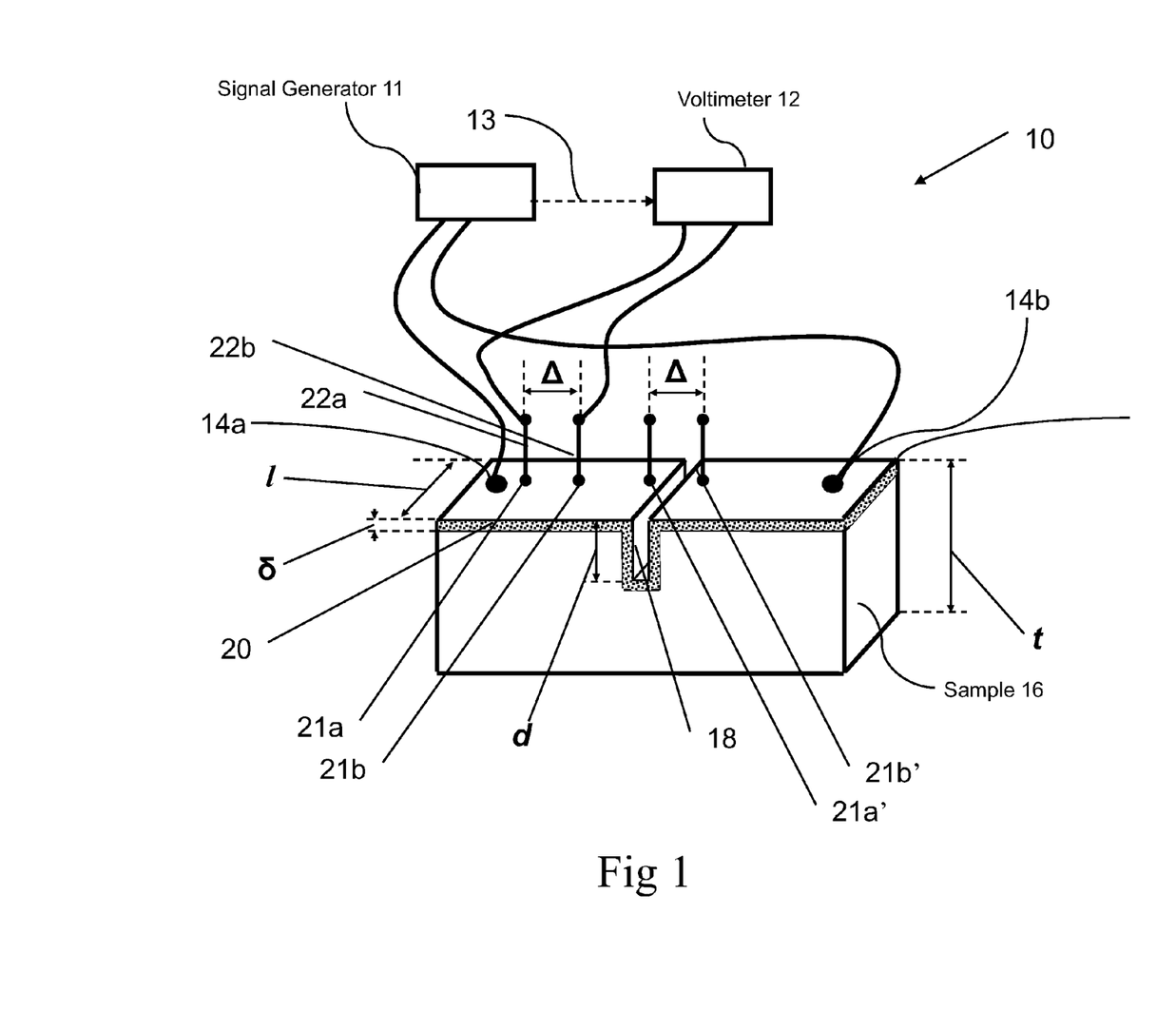
FIG. 1 schematically depicts measuring system for detecting and characterizing cracks in conductive samples according to the current invention.

FIG. 1 schematically depicts measuring system 10 used for detecting and characterizing cracks in conductive samples according to the current invention.

Sample 16 having width/and thickness t is shown here with a crack 18 penetrating from its upper surface 17. Crack 18, having depth d is narrow in one dimension so it may be hard to detect it visually and it is hard to determine its depth d. However, crack 18 is wide in the other dimension and causes electrical discontinuity to electric current flowing on upper surface 17. Although crack 18 appears: straight; encompassing the entire width of the sample width, and perpendicular to both upper surface and the sample long axis, it needs not be such. The methods of the current invention may work for cracks with other shapes.

Signal generator 11 is connected to two contacts 14a and 14b which make electrical contacts with upper surface 17 of sample 16.

Due to the skin effect, the alternating current supplied to the sample by signal generator 11 is confined to layer 20 having skin thickness δ.

Moving probes 22a and 22b make electrical contact with upper surface 17 of sample 16 at locations 21a and 21b respectively, wherein locations 21a and 21b are separated by a gap of constant length Δ.

Probes 22 are connected to voltmeter 12. Preferably, voltmeter 12 is a lock-in amplifier synchronized to signal generator 11 by the optional synchronization connection 13.

When probes 22 are in locations 21a and 21b, the voltage measured by voltmeter 12 is defined as $V_1$.

When probes 22 are moved to new locations 21a' and 21b', wherein the probes are on different sides of crack 18, voltmeter 12 measures voltage defined as $V_2$.

Proper location of probes for measuring $V_2$ may be determined by scanning probes 22 and identifying a maximum in the measured $V_2$.

Alternating current potential drop (ACPD) is a nondestructive technique used for mapping the depth of a crack by measuring the surface voltage adjacent to this crack. [1-4]

When an AC is passed through a good conductor, the displacement current may be neglected (σ>>ωε)) and the distribution of the electric field in the part is obtained according to Helmholtz Equation: [5-7]

$$\nabla^2 E = \mu\sigma\frac{\partial E}{\partial t} \quad (1)$$

where E is the electric field, μ is the magnetic permeability, and σ is the electric conductivity.

When applying high frequency current into metal, the current tends to concentrate in a thin layer close to the surface and flows along the metal surface (skin effect). The skin thickness δ, depends on the metal properties and the current frequency f, and is approximated by:

$$\delta = \frac{1}{(\pi\mu_r\mu_0\sigma f)^{1/2}} \quad (2)$$

where $\mu_r$ is the relative magnetic permeability and $\mu_0$ is the magnetic permeability of free space.

FIG. 1 shows the uniform flow of current in a skin of thickness δ normally incident on a crack of a uniform depth d and width w. The current is injected at point 14a and flows along the metal surface, down and up the crack 18, and out through point 14b. The voltage drop is measured by a probe whose contacts form a gap of constant length Δ. When placing the probe far from the crack, for example at locations 21a and 21b, a voltage $V_1$ is measured. When placing the probe across the crack, for example at locations 21a' and 21b', a voltage $V_2$ is measured. [1]

The problem simplifies to a thin skin problem when the following conditions are met:

$$t/\delta>10, \ d/\delta>10, \ w/\delta>10 \quad (3)$$

where t is the part thickness, d is the crack depth, and w is the crack length.

In thin skin, the electrical field is assumed to be uniform in the region of interest around the crack. This means that the wavelength along the surface λ>>d, w, and Δ.

The assumption is probably reasonable for a broad crack (w=d), but for a very arrow crack (w<<d) the field inside the crack might be partially shielded.

For the thin skin, the crack depth is approximated by [3]

$$d = \frac{\Delta}{2}\left(\frac{V_2}{V_1} - 1\right) \quad (4)$$

Eq. (4) is referred to as the one-dimensional (1D) approximation of the crack depth and gives an excellent estimate for the thin skin case.

By contrast, the thick skin case is met when at least one of the requirements for the thin skin fails to be fulfilled.

For a thick skin, an approximation for the crack depth is given by [8-10]

$$d = \frac{\Delta}{2}\left(\frac{V_1}{V_2}\right)^{1/2}\left(\frac{V_2}{V_1} - 1\right) \quad (5)$$

Eq. (5) derived from calculating the surface electric potential. The potential is of opposite sign on each side of the crack, so that there is a jump in the potential across the crack. [8-10]

In practice Eq. (5) provides a lower limit of the crack depth.

So far, the thin skin approximation is well established and supported experimentally. The thick skin solution is a modification (adjustment) of the thin skin solution that requires cumbersome experimental calibration. But the main problem remains that there is no seamless transition between these two approximations that would allow a systematic variation of the experimental parameters. Consequently, initial "guesswork" is required to determine which skin thickness is most appropriate to the problem at hand.

It is an aspect of the current invention to provide a global solution which can predict the crack depth for all cases from thin to thick skin in a seamless manner. The solution according to the current invention provides a good estimate for all probe distances Δ, especially at short distances, because the sensitivity for crack depth increases as the probe distance decreases.

Maxwell's equations were solved numerically for various combinations of skin and crack depths using a finite element model (ANSYS)[11]. The analyzed problem consisted of a metallic conductor with a rectangular cross section area containing a surface crack of uniform depth. A uniform sinusoidal current was applied remotely from the crack, parallel to the surface. The current frequency was varied to model all the cases from thin to thick skin.

Near the corner of the crack beginning at a distance of about 2δ from the crack, the current decreases to zero. A detailed characterization of the current as a function of the distance from the crack (not shown here), shows that the functional relationship is exponential.

This phenomenon, subsequently referred to as the "corner effect," occurs in all the analyzed cases, irrespective of the skin thickness. For the thin skin, the corner effect is very small because its length (2δ) is short compared to the crack depth. The corner effect may therefore be neglected for all practical purposes in this thin skin configuration. At the internal bottom part of the crack, the current increases significantly. This effect stems from the geometrically sharp corners of the present model and is not observed for blunt cracks. This local effect has no real influence on the measured voltage characteristics.

At distances greater than 2δ, the current density becomes constant, so that the voltage becomes linearly dependent on the distance. The 1D approximation thus gives excellent results when all the thin skin conditions are met.

For the thick skin case, the same phenomenon occurs, but the corner effect is no longer negligible because its characteristic length (2δ) is now of the order of the crack length.

Based on these results, we seek a solution based on the 1D solution [Eq. (4)] which also takes into account the corner effect. Subtraction of the 1D voltage solution from the numerically determined solution yields an exponential relationship between the measured voltages ratio and the normalized probe distance. Therefore, it can be assumed that the corner effect behaves exponentially. By analogy with Eq. (4), the sought solution should have the following form:

$$\frac{V_2}{V_1} = \frac{\Delta + 2d - F_1(\Delta, \delta) - F_2(d, \delta)}{\Delta} \quad (6)$$

where the functions $F_1$ and $F_2$ represent the corner effect.

Therefore, $F_1$ and $F_2$ are dominant for the thick skin and negligible for the thin skin.

The function $F_1$ compensates for the decrease of the voltage on the specimen surface and is dependent on $\Delta$ and $\delta$.

The function $F_2$ compensates for the decrease of the voltage on the crack plane and is therefore dependent on both d and δ.

In all the cases, these functions should have a significant effect at a distance of up to 2δ from the crack, so that the exponential term should also include δ in the denominator.

The proposed empirical equations which include the corner effect is thus given by $$F_1(\Delta, \delta) = \Delta \cdot \exp\left[-\frac{\Delta/2 + \delta}{\delta}\right] \quad (7)$$

$$F_2(d, \delta) = 2 \cdot d \cdot \exp\left[-\frac{d + \delta}{\delta}\right] \quad (8)$$

Simulations were done on different materials (aluminum σ=3. 107 s/m) and stainless steel σ=1.4 106 s/m), for different crack depth (0.2t, 0.6t), and different frequencies (70 Hz-200 kHz) which define the skin depth (0.1·t–t), and the same of corner effect phenomenon was observed.

Figure 3:
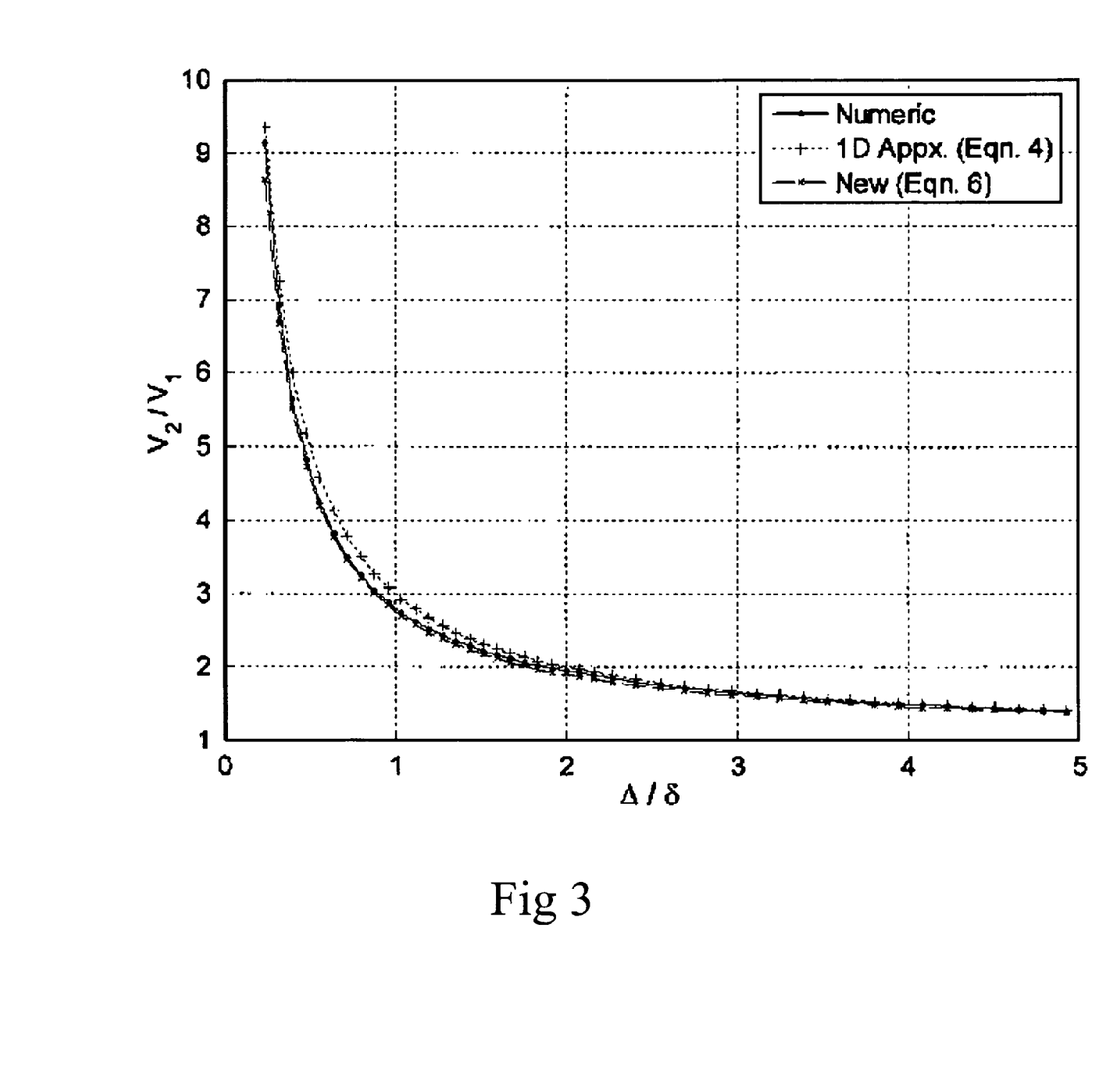
FIG. 3 shows a graph of the ratio $V_2/V_1$ calculated using: numerical results from finite element model; 1D approximation known in the art from Eq. (4); and using Eq. (6) acceding to the current invention, all plotted against $\Delta/\delta$ for a thick skin case: $t/\delta=50/30$; $d/\delta=10/30$.
Figure 4:
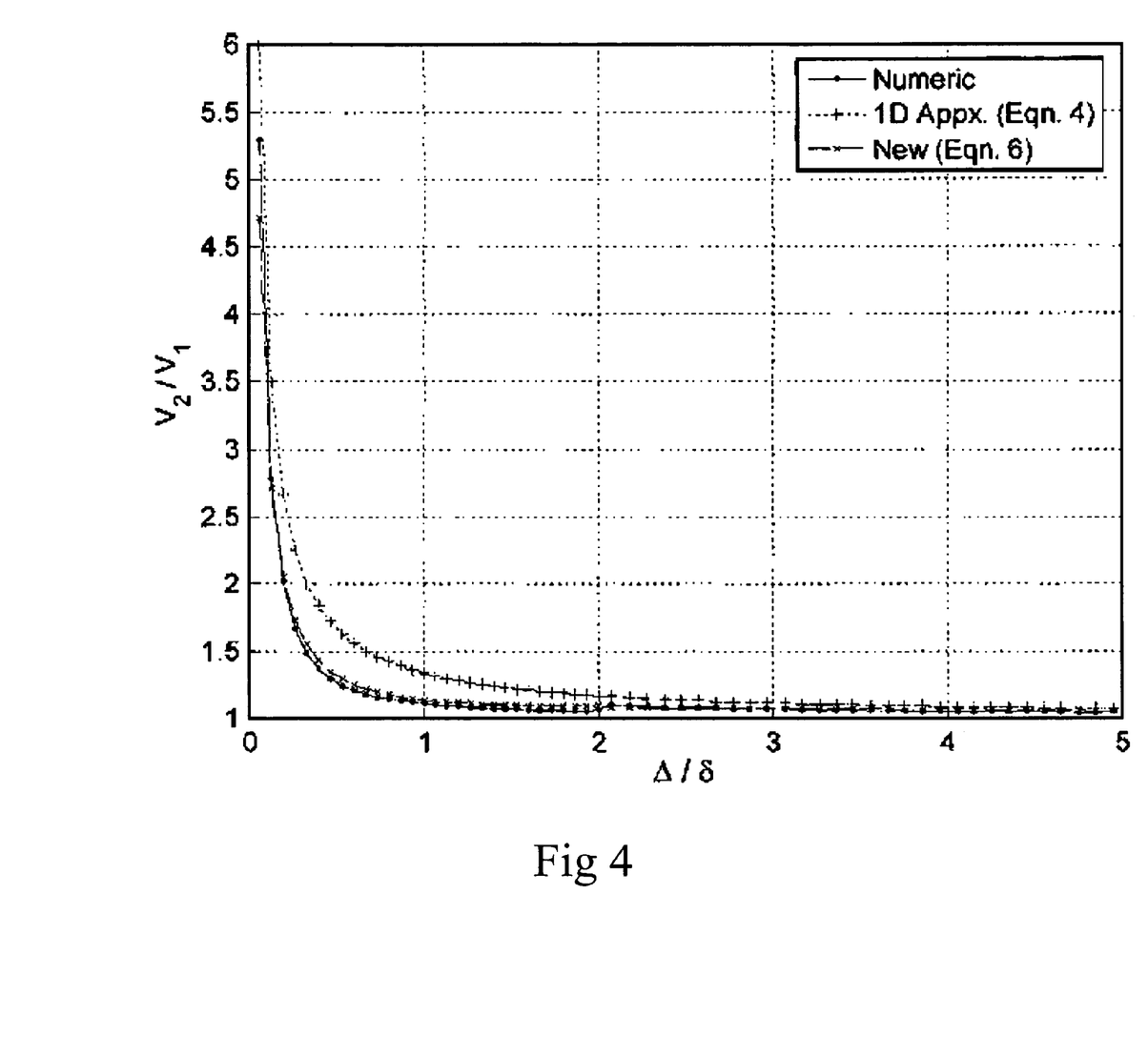
FIG. 4 shows a graph of the ratio $V_2/V_1$ calculated using: numerical results from finite element model; 1D approximation known in the art from Eq. (4); and using Eq. (6) acceding to the current invention, all plotted against $\Delta/\delta$ a thick skin case: $t/\delta=50/30$; $d/\delta=10/30$.
Figure 5:
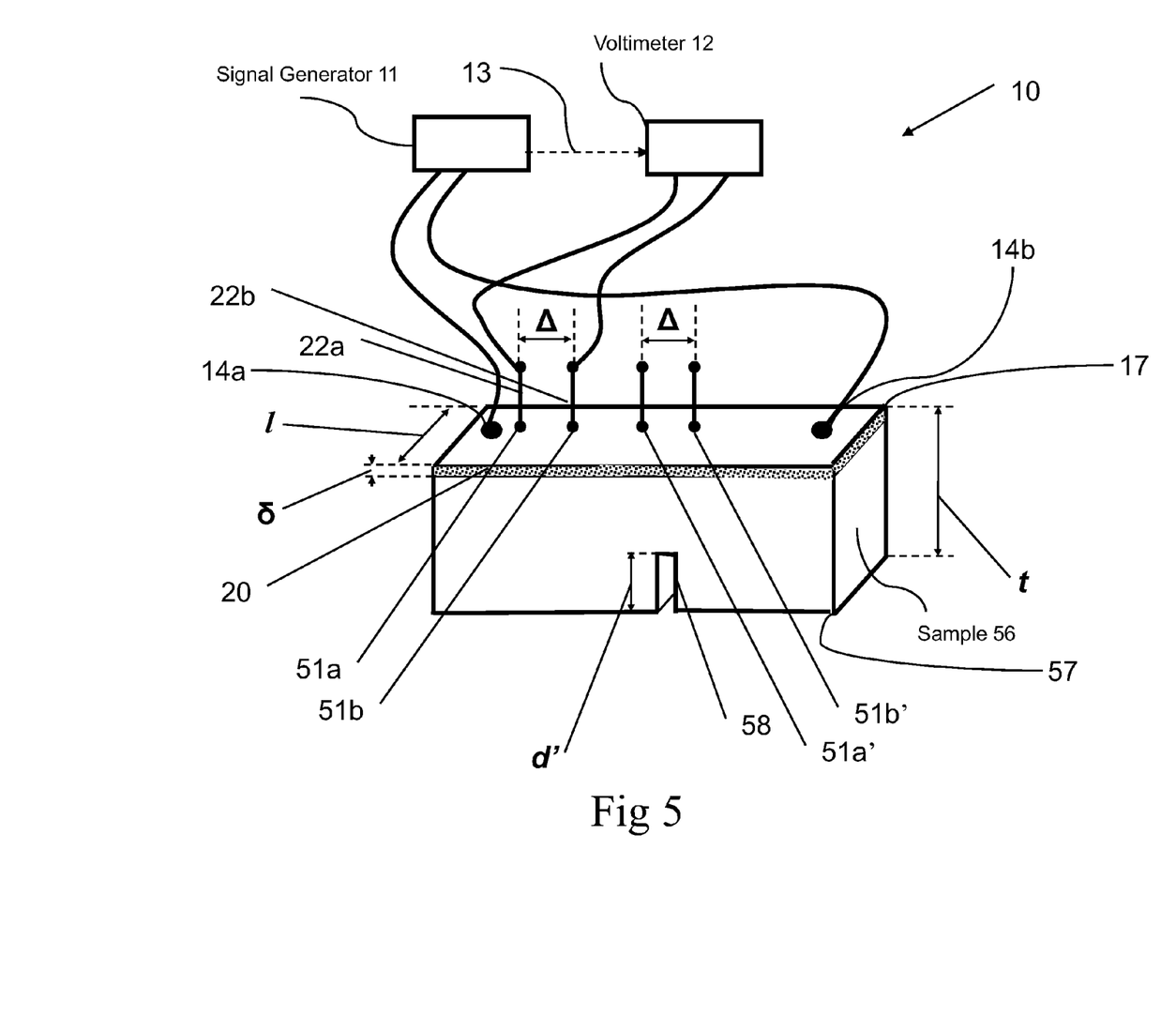
FIG. 5 schematically depicts the measuring system for detecting and characterizing of bottom cracks in conductive samples according to another embodiment of the current invention.

Comparisons between the simulation results, 1D approximation, and the proposed solution are shown in FIGS. 3-5 for different frequencies and different crack size. These figures show typical results for a thin and thick skin case.

Figure 2:
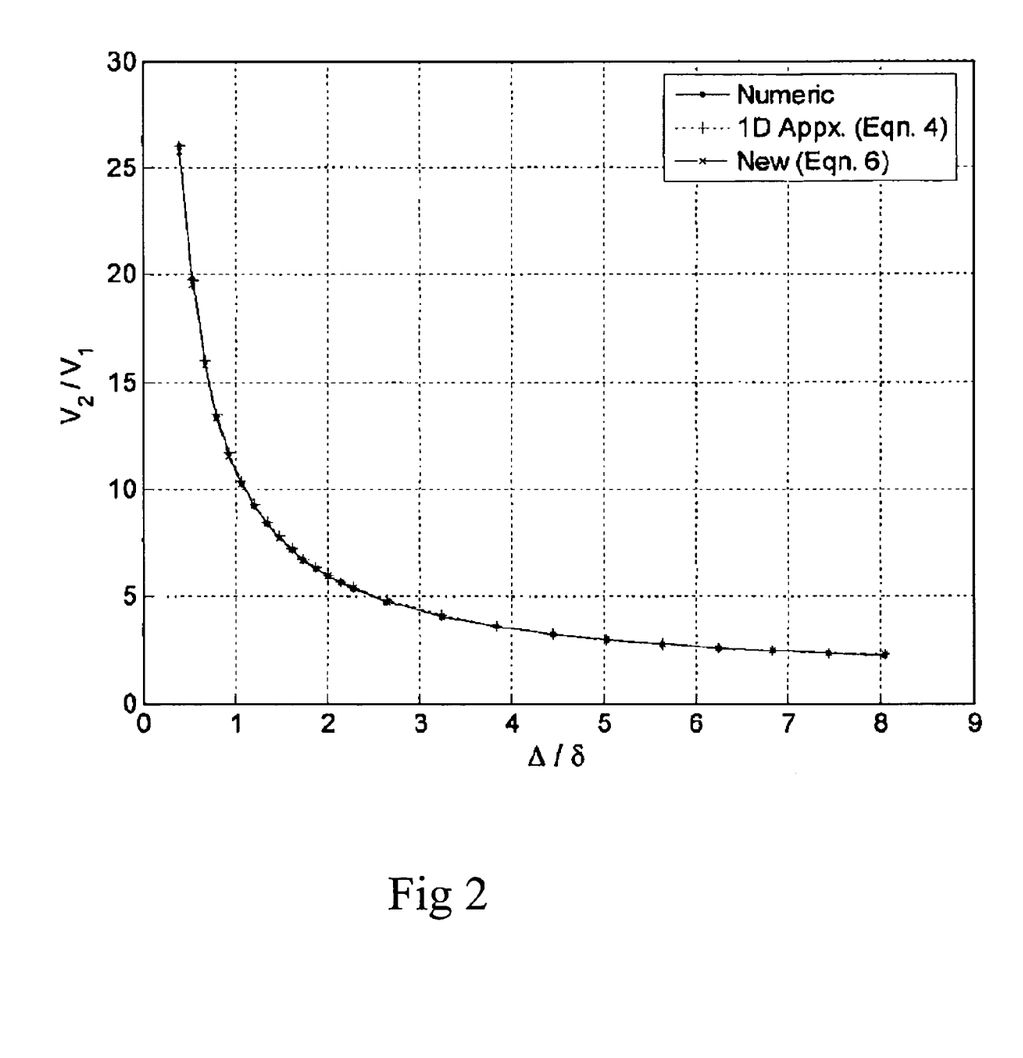
FIG. 2 shows a graph of the ratio $V_2/V_1$ calculated using: numerical results from finite element model; 1D approximation known in the art from Eq. (4); and using Eq. (6) acceding to the current invention, all plotted against $\Delta/\delta$ for the thin skin case: $t/\delta=50/3$; $d/\delta=30/3$.

FIG. 2 shows a graph of the ratio $V_2/V_1$ calculated using: numerical results from finite element model, 1D approximation known in the art from Eq. (4); and Eq. (6) acceding to the current invention, plotted against Δ/δ for the thin skin case: t/δ=50/3; d/δ=30/3.

A very good fitting can be noted, as expected, between the 1D approximation [Eq. (4)], the numerical results and the new approximation [Eq. (6)].

FIG. 3 shows a graph of the ratio $V_2/V_1$ calculated using: numerical results from finite element model, 1D approximation known in the art from Eq. (4); and Eq. (6) acceding to the current invention, plotted against Δ/δ for a thick skin case: t/δ=50/5; d/δ=10/3.

FIG. 4 shows a graph of the ratio $V_2/V_1$ calculated using: numerical results from finite element model, 1D approximation known in the art from Eq. (4); and Eq. (6) acceding to the current invention, plotted against Δ/δ a thick skin case: t/δ=50/30; d/δ=10/30.

In FIGS. 3 and 4 it can be observed that, for the same crack depth, the numerical results and the 1D approximation are increasingly divergent as the frequency decreases (thick skin case). The new solution [Eq. (6)] gives a very good fitting for all these cases.

From these results we conclude that the proposed Eq. (6) gives an excellent prediction of the voltage variation in a specimen with a uniform depth crack for all frequencies.

This equation is based on the 1D approximation for thin skin, with the addition of the corner effect at a distance of 2δ from the crack. The corner effect occurs at all frequencies, but it is dominant for thick skin and may be neglected for thin skin.

Equation (6) is of a high practical interest as it eliminates the need for a priori assessment of the skin condition with the appropriate thin or thick skin solution.

According to an embodiment of the invention, probes 22 are used for scanning the sample keeping constant gap between their tips, while signal generator 11 is supplying alternating current and signals from voltmeter 12 is registered.

Location of a crack is identified by increase of the voltage when probes 22 are at two sides of the crack. At that location, $V_2$ is noted. Value of $V_1$ is measured by displacing the probes so both contacts are at the same side and removed from the crack. Optionally, an average is taken from measurements of $V_1$ on either sides of the crack.

At least one measurement of $V_2(f_0)$ and $V_1(f_0)$ is taken at a known frequency $f_0$, and preferably, plurality of measurements of $V_2(f_i)$ and $V_1(f_i)$ are taken at plurality of frequencies $f_i$ and the ratios $[V_2/V_1](f_i)$ are calculated.

Knowing the electrical parameters of sample material, and the system geometry, the calculated experimental ratios $[V_2/V_1](f_i)$ are fitted to Eq. (6) using a single fitting parameter d. The best fit gives estimation to the depth of the crack. If one measurement was taken at frequency $f_0$, Eq. (6) may be numerically solved using methods known in the art.

Another aspect of the invention is to provide a method to allow detection locating and characterization of flaws below the surface, or on the surface other than the inspected surface.

FIG. 5 schematically depicts the measuring system 10 of FIG. 1 as used for detecting and characterizing of bottom cracks in conductive samples according to another embodiment of the current invention. In this figure, all elements of the measuring system and the sample are the same as in FIG. 1 except the location of the cracks.

Sample 56 having width/thickness t is shown here with a crack 58 penetrating from its lower surface 57. Crack 58, having depth d' may be hard to detect visually and it is hard to determine its depth d' as it does not penetrate the upper surface 17. Crack 58 is narrow compared with distance Δ between probes 22 and is wide in the other dimension. Although crack 58 appears: straight; encompassing the entire width of the sample and perpendicular to both upper surface and the sample long axis, it needs not be such. The methods of the current invention may work for cracks with other shapes.

When probes 22 are in locations 51*a* and 51*b*, the voltage measured by voltmeter 12 is defined as $v_1$. When probes 22 are moved to new locations 51*a*' and 51*b*', wherein the probes are above different sides of crack 58, voltmeter 12 measures voltage defined as $v_2$.

Locations 51a' and 51b' may be determined by a maximum in $v_2$ while probes 22 scan across the sample.

Figure 6:
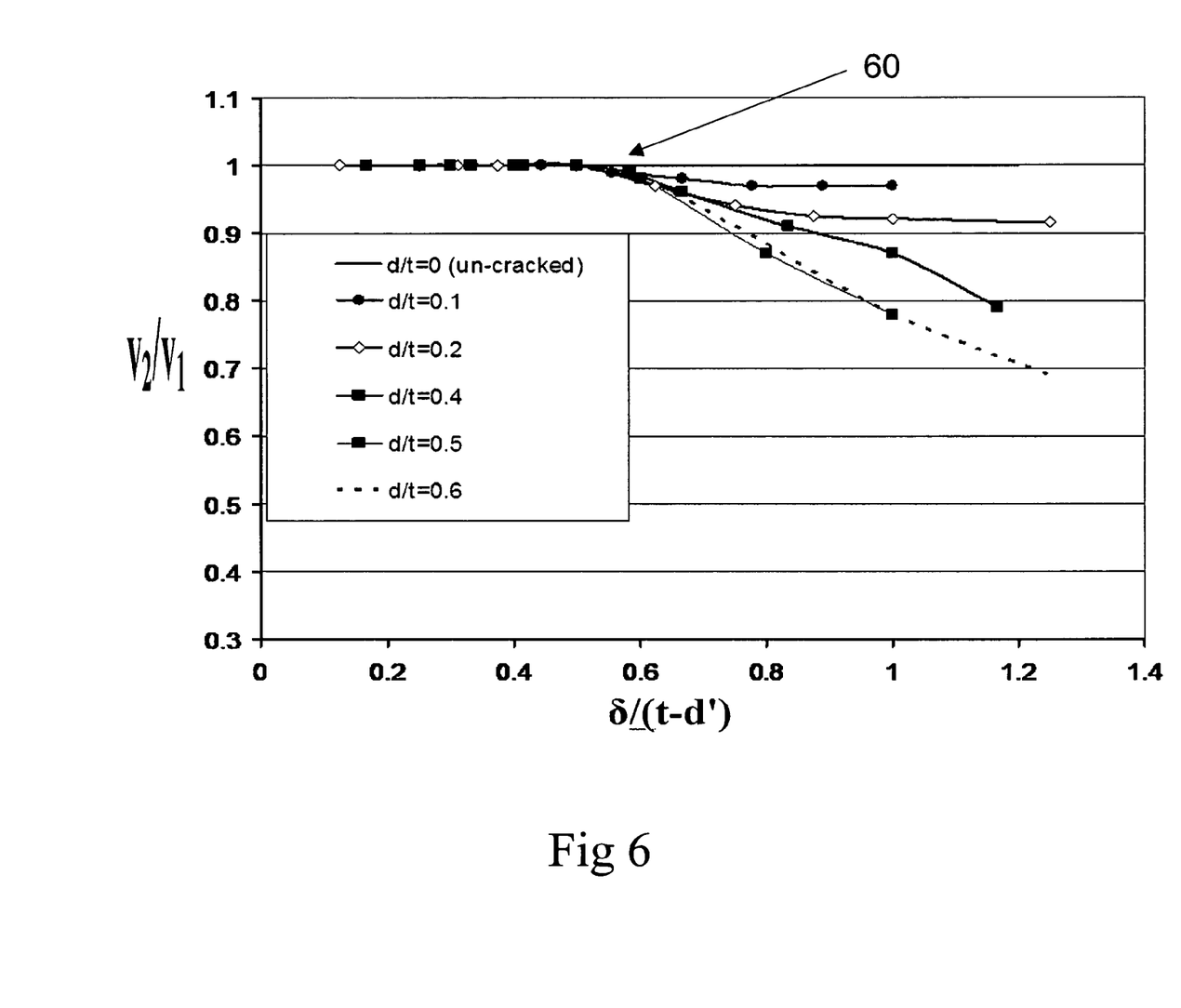
FIG. 6 shows the experimentally measured ratio of the voltage drop cased by a bottom crack to reference voltage drop, plotted as a function of $\delta/(t-d')$, for several $t/d'$ ratios using probes separated by distance of 5 mm.

FIG. 6 shows the ratio between the voltage drop cased by a bottom crack $v_2$ to reference voltage drop $v_1$, plotted as a function of $\delta/(t-d')$ for several t/d' ratios. Ratios of $v_2/v_1$ were calculated from measured signals using probes separated by distance of $\Delta=5$ mm.

It is clear to see that for un-cracked sample (d'=d'/t=0) there is no effect on $v_2$ and the ratio $v_2/v_1=1.0$ for all values of $\delta$.

For cracked samples, the departure from straight line is larger for deeper cracks.

Specifically, it should be noted that the point 60 where each of the graphs departs from horizontal is at $\delta/(t-d') \sim 0.5$.

Thus, according to an embodiment of the invention, estimation for the depth of bottom crack may be obtained by performing the following steps:

Applying alternating current to a sample.

Measuring voltage drop $v_1(f_i)$ between the probes for plurality of frequencies $f_i$ where probes are located remove from the bottom crack Positioning the probes so that probes are above different sides of the bottom crack and measuring voltage drop $v_2(f_i)$ between the probes for same plurality of frequencies $f_i$.

Proper location of probes for measuring $v_2$ may be determined by scanning probes 22 and identifying a maximum in the measured $v_2$.

For each frequency $f_i$, calculating the ratio $[v_2/v_1](f_i)$

For each frequency $f_i$, calculating $\delta(f_i)$ based on electrical parameters of sample material.

Plotting the ratio $[v_2/v_1](f_i)$ as a function of $\delta(f_i)$.

Estimating the value of $\delta_0$ where the ratio $v_2/v_1$ start departing from horizontal.

Calculating the estimated depth d' of back crack from the equation: $d'=t-2\delta_0$ wherein t is the sample thickness.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub combination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. An improvement to a method for non destructive testing of an object by determination of depth of surface penetrating crack in said object that comprises applying alternating current to a sample; measuring voltage drop $V_1(f)$ between two probes separated by a gap of distant $\Delta$ and making electrical contact with the surface of the sample for at least one frequency f, wherein said probes are located remove from the surface penetrating crack; measuring voltage drop $V_2(f)$ between two probes separated by a gap of distance $\Delta$ and making electrical contact with said surface of said sample, for at least same frequency f, wherein said probes are located at different sides of said surface penetrating crack; and calculating $\delta$ based on electrical parameters of said samplers material, the improvement comprising the steps of:

determining the depth d of said surface penetrating crack from the equation:

$$\frac{V_2(f)}{V_1(f)} = \frac{\Delta + 2d - F_1(\Delta, \delta) - F_2(d, \delta)}{\Delta},$$

wherein $$F_1(\Delta, \delta) = \Delta \cdot \exp\left[-\frac{\Delta/2 + \delta}{\delta}\right],$$

and $$F_2(d, \delta) = 2 \cdot d \cdot \exp\left[-\frac{d + \delta}{\delta}\right],$$

and wherein:

$$\delta = \frac{1}{(\pi \mu_r \mu_0 \sigma f)^{1/2}},$$

where $\mu_r$ is the
relative magnetic permeability; $\mu_0$ is the magnetic permeability of free space; $\sigma$ is the electric conductivity; f is the frequency; and
rejecting said object based on said determined depth.

2. The improvement to a method for non destructive testing of an object of claim 1 wherein the step of determining the depth d of said surface penetrating crack from the equation $$\frac{V_2}{V_1} = \frac{\Delta + 2d - F_1(\Delta, \delta) - F_2(d, \delta)}{\Delta}$$

comprises numerically solving said equation.

3. The improvement to a method for non destructive testing of an object of claim 1 and further comprising:
scanning said two probes separated by a gap of distant $\Delta$ and making electrical contact with said surface of said sample along said surface, while measuring said voltage drop;
determining the location of said surface penetrating crack by finding a maximum of said measured voltage drop; and
assigning the value $V_2(f)$ to the said maximum of said measured voltage drop.

4. The improvement to a method for non destructive testing of an object of claim 1 and further comprising:
measuring voltage drop $V_1(f_i)$ between probes separated by a constant gap and making electrical contact with said surface of said sample, for plurality of frequencies $f_i$, where probes are located remove from the bottom crack;
measuring voltage drop $V_2(f_i)$ between probes separated by a constant gap and making electrical contact with said surface of said sample, for same plurality of frequencies $f_i$, where probes are located at different sides of said surface penetrating crack; and determining the depth d of said surface penetrating crack from the set of equations:

$$\frac{V_2(f)}{V_1(f)} = \frac{\Delta + 2d - F_1(\Delta, \delta) - F_2(d, \delta)}{\Delta}$$

evaluated for frequencies $f_i$.

5. The improvement to a method for non destructive testing of an object of claim 4 wherein the step of determining the depth d of said surface penetrating crack comprises fitting a single fifing parameter d to said set of equations.

6. An improvement to a method for non destructive testing of a sample by determination of the depth of a crack located near the bottom surface of a said sample that comprises applying alternating current to a sample; measuring voltage drop $v_1(f_i)$ between two probes separated by a gap of distant $\Delta$ and making electrical contact with the top surface of the sample for plurality of frequencies $f_i$ wherein said probes are located remove from the bottom crack; measuring voltage drop $v_2(f_i)$ between two probes separated by a gap of distant $\Delta$ and making electrical contact with said top surface of the sample for the same plurality of frequencies $f_i$ wherein said probes are located above different sides of the bottom crack, the improvement comprising the steps of:

for each frequency $f_i$, calculating the ratio $[v_2/v_1](f_i)$ by dividing $v_2(f_i)$ by $v_1(f_i)$;

for each frequency $f_i$, calculating $\delta(f_i)$ based on electrical parameters of sample material;

plotting the ratio $[v_2/v_1](f_i)$ as a function of $\delta(f_i)$;

from said plot of the ratio $[v_2/v_1](f_i)$ as a function of $\delta(f_i)$, estimating the value of $\delta_0$ where the ratio $v_2/v_1$ start departing from horizontal;

calculating the determined depth d' of back crack from the equation: $d'=t-2\delta_0$ wherein t is the sample thickness; and rejecting said sample based on said determined depth.

7. The improvement to a method for non destructive testing of a sample according to claim 6 and further comprising:

scanning said two probes separated by a gap of distant $\Delta$ and making electrical contact with said top surface of said sample along said top surface, while measuring said voltage drop;

determining the location of said crack by finding a maximum of said measured voltage drop; and assigning the value $v_2(f)$ to the said maximum of said measured voltage drop.

* * * * *